(12) United States Patent
Gavalis et al.

(10) Patent No.: US 10,709,315 B2
(45) Date of Patent: Jul. 14, 2020

(54) APPARATUSES AND METHODS FOR ENDOSCOPIC CONNECTION

(71) Applicant: HOYA Corporation, Tokyo (JP)

(72) Inventors: Robb Morse Gavalis, Westborough, MA (US); Christopher Kadamus, West Roxbury, MA (US); Anh Minh Do, Munich (DE)

(73) Assignee: Hoya Corporation, Tokyo (JP)

( * ) Notice: Subject to any disclaimer, the term of this patent is extended or adjusted under 35 U.S.C. 154(b) by 505 days.

(21) Appl. No.: 15/581,049

(22) Filed: Apr. 28, 2017

(65) Prior Publication Data

US 2018/0310806 A1     Nov. 1, 2018

(51) Int. Cl.
*A61B 1/00* (2006.01)
*A61B 17/00* (2006.01)
(Continued)

(52) U.S. Cl.
CPC ...... *A61B 1/00128* (2013.01); *A61B 1/00133* (2013.01); *A61B 1/00137* (2013.01); *A61B 1/018* (2013.01); *A61B 10/04* (2013.01); *A61B 17/00234* (2013.01); *A61B 2017/0034* (2013.01); *A61B 2017/00455* (2013.01); *A61B 2017/00477* (2013.01); *A61B 2017/00486* (2013.01); *A61B 2017/347* (2013.01)

(58) Field of Classification Search
None
See application file for complete search history.

(56) References Cited

U.S. PATENT DOCUMENTS

| 5,910,105 A | 6/1999 | Swain et al. |
|---|---|---|
| 6,228,059 B1 | 5/2001 | Astarita |
| (Continued) | | |

FOREIGN PATENT DOCUMENTS

| JP | H03195547 | 8/1991 |
|---|---|---|
| WO | WO 2010/023460 A1 | 3/2010 |

OTHER PUBLICATIONS

International Search Report and Written Opinion for International Application No. PCT/162018/000488 filed Apr. 27, 2018, dated Sep. 3, 2018.

*Primary Examiner* — Timothy J Neal
(74) *Attorney, Agent, or Firm* — Finnegan, Henderson, Farabow, Garrett & Dunner, LLP

(57) ABSTRACT

Embodiments of the present disclosure are directed to apparatuses, devices, and methods for connecting a device to an endoscope. In one implementation, an apparatus for connecting a device to an endoscope includes a multi-tined connector and a locking sleeve. The multi-tined connector is configured to engage with a port of an endoscope having a non-circular flange. The multi-tined connector includes a body portion and a plurality of tines connected to the body portion. The body portion has a lumen axially extending therethrough and an outer locking interface. The tines are radially deflectable, have outer tapered surfaces, and operate between an engaged position and a disengaged position, wherein in the engaged position, the tines engage with the port. The locking sleeve operates between a locked position and an unlocked position. In the locked position, the locking sleeve holds the tines in the engaged position, and in the unlocked position, the locking sleeve leaves the tines in the disengaged position.

20 Claims, 12 Drawing Sheets

(51) Int. Cl.
    *A61B 1/018*     (2006.01)
    *A61B 10/04*     (2006.01)
    *A61B 17/34*     (2006.01)

(56) References Cited

U.S. PATENT DOCUMENTS

| | | |
|---|---|---|
| 6,229,576 B1 | 10/2001 | Ouchi |
| 6,796,586 B2 | 9/2004 | Werth |
| 7,927,271 B2 | 4/2011 | Dimitriou et al. |
| 8,409,243 B2 | 4/2013 | Chu |
| 8,460,176 B2 | 6/2013 | McGrath |
| 8,603,047 B2 | 12/2013 | Stroup |
| 8,974,441 B2 | 3/2015 | Oskin et al. |
| 9,386,963 B2 | 7/2016 | Ryan et al. |
| 2004/0006256 A1 | 1/2004 | Suzuki et al. |
| 2007/0270640 A1* | 11/2007 | Dimitriou .......... A61B 1/00128 600/106 |
| 2011/0065995 A1 | 3/2011 | Cushner et al. |
| 2012/0226101 A1 | 9/2012 | Tinkham et al. |
| 2012/0253128 A1 | 10/2012 | Yamane |
| 2014/0265313 A1* | 9/2014 | Durr .................. A61B 1/00128 285/305 |
| 2015/0119641 A1 | 4/2015 | Yamada |
| 2016/0262601 A1 | 9/2016 | Viebach et al. |

\* cited by examiner

APPARATUSES AND METHODS FOR ENDOSCOPIC CONNECTION

BACKGROUND

Technical Field

The present disclosure generally relates to endoscopic systems and methods of use. More particularly, and without limitation, the disclosed embodiments relate to apparatuses, devices, and methods for connecting or mounting a device to an accessory port of an endoscope.

Background Description

Endoscopic procedures are widely performed to diagnose or treat pancreaticobiliary and gastrointestinal diseases. An endoscope typically has one or more flexible elongated channels, such as a working or biopsy channel, and one or more accessory ports, such as a biopsy port. The flexible elongated channels extend along the length of the endoscope to allow passage of accessories and devices into a patient to perform diagnostic and/or therapeutic procedures. The biopsy ports are provided near the proximal end of an endoscope. Typically, a device is attached to or passes through a biopsy port, and is then inserted into a working channel of the endoscope to approximate or reach a desired treatment site in the patient. For many endoscopic diagnostic or treatment procedures, it is desirable to precisely locate and/or maintain the distal end of a device at a particular position and/or orientation relative to the distal end of the endoscope or a desired treatment site.

Many biopsy ports of endoscopes are Luer ports and the attachment of a device to the biopsy port is typically via Luer-Lok style connection. Luer-Lok style connection is commonly used in small-scale fluid and pressure based connections, for example, in pressure based applications having pressures below about 50 psi. Such connection, however, tend to loosen or wobble when torque, axial forces, and/or off-axis moment forces are applied to the device. In addition, many devices have a long shaft that extends through the elongated channel of the endoscope. When a physician rotates such a device to connect the device to the biopsy port or to position or orient the distal end of the device, rotational torque can build up in the shaft of the device. The built-up torque in the shaft can act to loosen the Luer-Lok style connection in the opposite direction.

The loosening of the Luer-lok style connection can undesirably lead to poor connection, fluid leaking at the biopsy port, displacement of the distal end of the device from a desired treatment site, and/or disconnection of the device from the biopsy port. The potential loosening or failure of the Luer-Lok style connection burdens a physician with frequent checking and adjustment of the connection of the device to the biopsy point to maintain stability and security of the device as well as the position and/or orientation of the distal end of the device. Additionally, the potential loosening connection makes it more difficult for the physicians to control the distal end of the device.

Therefore, an improved apparatus or system is needed that allows accessories and devices to be securely connected to the biopsy port of an endoscope. Such an apparatus or system is capable of reducing the time taken for a physician to perform an endoscopic procedure and increasing the effectiveness of the procedure.

SUMMARY

The embodiments of the present disclosure include apparatuses, systems, and methods for connecting devices to a biopsy port of an endoscope. Advantageously, the exemplary embodiments allow for stable and secured connection of a device to the biopsy port, with the goal of improving the efficiency and effectiveness of endoscopic procedures.

According to an exemplary embodiment of the present disclosure, an apparatus for connecting a device to an endoscope is described. The apparatus includes a multi-tined connector and a locking sleeve. The multi-tined connector is configured to engage with a port of an endoscope having a non-circular flange. The multi-tined connector includes a body portion and a plurality of tines connected to the body portion. The body portion has a lumen axially extending therethrough and an outer locking interface. The tines are configured to be radially deflectable, have outer tapered surfaces, and operate between an engaged position and a disengaged position, wherein in the engaged position, the tines engage with the port. The locking sleeve operates between a locked position and an unlocked position. The locking sleeve includes an inner engagement surface and an inner locking interface configured to engage with the outer locking interface. In the locked position, the locking sleeve holds the tines in the engaged position, and in the unlocked position, the locking sleeve leaves the tines in the disengaged position.

According to a further exemplary embodiment of the present disclosure, an endoscopic system having an apparatus for connecting a device to an endoscope is described. The apparatus includes a multi-tined connector and a locking sleeve. The multi-tined connector is configured to engage with a port of an endoscope having a non-circular flange. The multi-tined connector includes a body portion and a plurality of tines connected to the body portion. The body portion has a lumen axially extending therethrough and an outer locking interface. The tines are configured to be radially deflectable, have outer tapered surfaces, and operate between an engaged position and a disengaged position, wherein in the engaged position, the tines engage with the port. The locking sleeve operates between a locked position and an unlocked position. The locking sleeve includes an inner engagement surface and an inner locking interface configured to engage with the outer locking interface. In the locked position, the locking sleeve holds the tines in the engaged position, and in the unlocked position, the locking sleeve leaves the tines in the disengaged position.

According to a yet further exemplary embodiment of the present disclosure, a connector for engaging with a port having a non-circular flange is described. The connector includes a multi-tined connector and a locking sleeve. The multi-tined connector is configured to engage with a port of an endoscope having a non-circular flange. The multi-tined connector includes a body portion and a plurality of tines connected to the body portion. The body portion has a lumen axially extending therethrough and an outer locking interface. The tines are configured to be radially deflectable, have outer tapered surfaces, and operate between an engaged position and a disengaged position, wherein in the engaged position, the tines engage with the port. The locking sleeve operates between a locked position and an unlocked position. The locking sleeve includes an inner engagement surface and an inner locking interface configured to engage with the outer locking interface. In the locked position, the locking sleeve holds the tines in the engaged position, and in the unlocked position, the locking sleeve leaves the tines in the disengaged position.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

DETAILED DESCRIPTION

Figure 1:
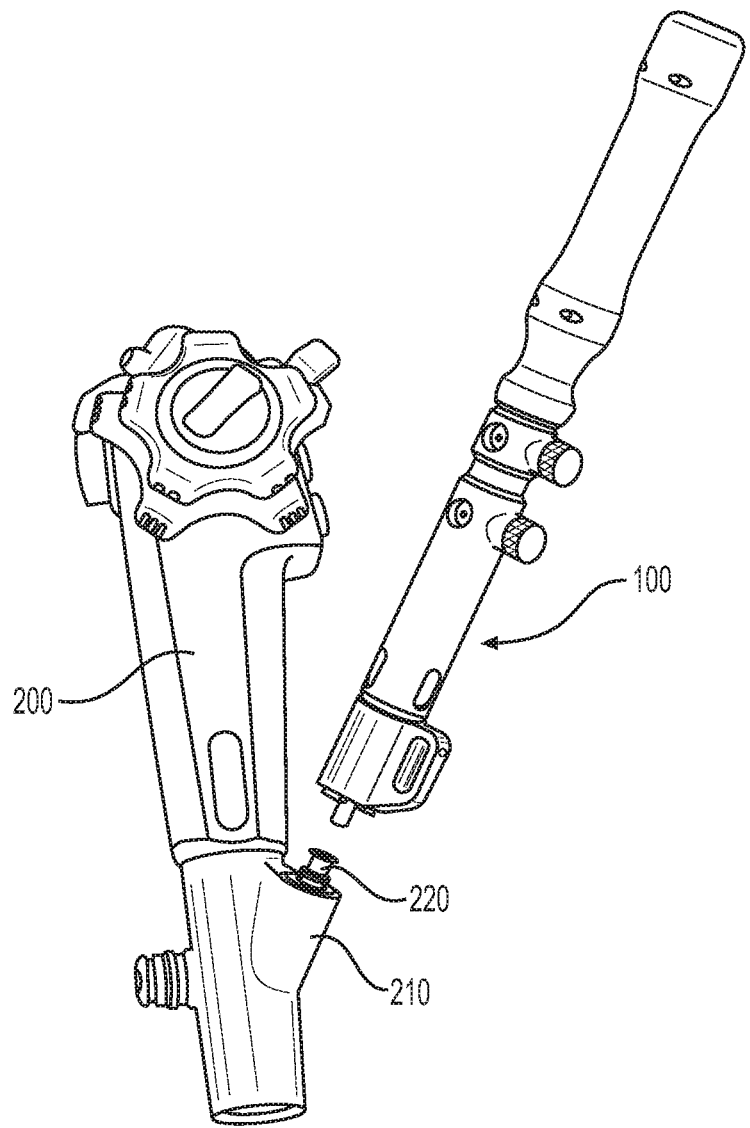
FIG. 1 is a perspective view of an exemplary apparatus for connecting a device to an exemplary port of an endoscope, according to embodiments of the present disclosure.

The disclosed embodiments relate to systems, apparatuses, and methods for efficient and effective connection of a device to a biopsy port of an endoscope. Embodiments of the present disclosure can be implemented in an endoscopic system for performing suitable diagnostic and/or therapeutic operations to one or more desired treatment sites in the gastrointestinal system, the respiratory system, the renal system, reproductive system, etc. Advantageously, embodiments of the present disclosure allow for stable and secure connection of a device to a biopsy port of an endoscope, allowing a physician to focus on the endoscopic procedure rather than checking and/or adjusting the connection, thereby improving the efficiency and effectiveness of the endoscopic procedure.

As described herein, an endoscope typically includes a distal end and a proximal end, and has an internal working channel extending between the distal end and the proximal end. A distal end may refer to the end of the endoscope closer to a treatment site in the body of a patient during an endoscopic procedure. A proximal end may refer to the end of the endoscope closer to a physician or a medical practitioner. A device is typically introduced into the working channel of the endoscope through a biopsy port provided at the proximal end of the endoscope until a distal end of the device approximates or reaches a desired treatment site.

According to an aspect of the present disclosure, an apparatus for connecting a device to a port of an endoscope is described. The port of the endoscope is a biopsy port provided at the proximal end of the endoscope that allows the device to be inserted into the working channel of the endoscope. The apparatus may be an integral component of a device to be inserted into the working channel of the endoscope or may be removably or fixedly connected to the device. Advantageously, the engagement of the apparatus with the port securely connects the device to the port and allows the distal end of the device to remain at a desired position and/or a desired orientation during an endoscopic procedure.

In some embodiments, a biopsy port of an endoscope includes a flange circumferentially formed around the top of the port. For example, the port may be a female Luer port having a non-circular flange with two protruding portions on opposite sides. The port may also include a circular lip on top of the flange. The port may further include a groove at the bottom where it connects to the endoscope. The apparatus may engage with the flange and/or the groove of the port to securely connect to the port.

According to a further exemplary embodiment of the present disclosure, the apparatus connecting a device to a port of an endoscope includes a multi-tined connector configured to be engaged with the port. The multi-tined connector may engage with the flange and/or the groove of the port of the endoscope. For example, the multi-tined connector includes a body portion and a plurality of tines connected to the body portion. The body portion of the multi-tined connector has a lumen axially extending therethrough for receiving a device. The tines are capable of being radially deflected inward or outward and operate between an engaged position and a disengaged position. In the engaged position, the tines are engaged with the port, securely connecting the device to the port. In the disengaged position, the tines are disengaged from the port.

According to a further exemplary embodiment of the present disclosure, the apparatus further includes a locking sleeve that operates between a locked position and an unlocked position to switch the tines between the engaged position and disengaged position. The locking sleeve may include an inner locking interface. The inner locking interface is configured to interlock with an outer locking interface of the body portion of the multi-tined connector, allowing the locking sleeve to switch between the locked and unlocked positions.

The locking sleeve may further include an inner engagement surface. The tines of the multi-tined connector may each have an outer tapered surface. When the locking sleeve switches from the unlocked position to the locked position, the inner engagement surface of the locking sleeve engages with the outer tapered surfaces of the tines, allowing the tines to radially deflect inward and engage with the port. When the locking sleeve switches from the locked position to the unlocked position, the inner engagement surface of the locking sleeve disengages from the outer tapered surfaces of the tines, causing the tines to radially deflect outward and disengage from the port.

In some embodiments, as the tines radially deflect inward, inner surfaces of the tines of the multi-tined connector may press against and form a friction fit with an outside wall of the port. Additionally or alternatively, when the port has a groove at the bottom, the tines may engage with and clamp onto the groove to form a secured connection. For example, the tines of the multi-tined connector may include inner ridges with inclined surfaces. As the locking sleeve switches from the unlocked position to the locked position, the tines radially deflect inward, causing the inner ridges of the tines to engage with and pull the groove of the port into the multi-tined connector, and to further tighten around the groove. The engagement of the tines with the groove of the port allows the apparatus to be securely locked onto the port of the endoscope.

Advantageously, the locking sleeve is capable of performing a binary switch between the locked and unlocked positions, improving the efficiency and effectiveness of connecting a device to an endoscope. The binary nature of the switch removes uncertainty as to if/when the locked or unlock position is reached. In some embodiments, the locking sleeve may also provide a visual cue that indicates the current position of the locking sleeve. The visual cue allows a physician to promptly secure the connection of the device, thereby reducing the possibility of undesirable displacement of the device and improving the efficacy of the endoscopic procedure.

According to an exemplary embodiment of the present disclosure, the apparatus further includes an anti-rotational key configured to prevent the apparatus from rotating around the port of an endoscope. The anti-rotational key may be an integral part of the multi-tined connector or may be securely fitted within the body portion of the multi-tined connector. For example, the anti-rotational key may be received within the lumen of the body portion of the multi-tined connector via friction fit, snap fit, etc. The anti-rotational key may have an elongated shape and a conduit therethrough to provide passage to a device into the port. The anti-rotational key may further include two opposing projections that, together with the surface of the lumen of the body portion, define a pocket for receiving the flange of the port. This anti-rotational key enables a physician to securely connect or disconnect a device using one hand, freeing up the other hand for holding or stabilizing the device or the endoscope. This in turn reduces the possibility of damaging or kinking the device during the connection or disconnection of the device.

The pocket for receiving the flange of the port may have an inner perimeter substantially matching the periphery of the flange of the port. In some embodiments, the engagement of the apparatus with the port can be achieved only when a non-circular flange of the port aligns with or fits in the pocket. Advantageously, this alignment or fitting results in the desired orientation of a device to be connected to the port, and allows a physician to connect and lock the device in the desired orientation conveniently using one hand. The alignment or fitting of the anti-rotational key further provides resistance to potential rotation of the apparatus and device around the port, thereby advantageously reducing rotational torque formed in the shaft of the device and thus preventing loosening of the connection of the device.

According to a further exemplary embodiment of the present disclosure, the apparatus includes a compressible seal. The compressible seal is positioned and/or fitted in the pocket formed by the anti-rotational key and the surface of the lumen of the body portion. When the multi-tined connector engages with the port, the compressible seal is compressed by the port, such as by the lip and/or flange of the port, thereby creating a fluid-tight seal about the port. When compressed, the compressible seal may also frictionally engage with the port, thereby further preventing the rotation of the device to be connected the port.

According to a further exemplary embodiment of the present disclosure, the apparatus includes a hollow conduit. The hollow conduit is at least partially received and fitted within the lumen of the body portion of the multi-tined connector. When the multi-tined connector is engaged with the port, the hollow conduit is at least partially received within the port, providing a passage for the device to be inserted into the port and the working channel of the endoscope. Advantageously, the hollow conduit provides a guide for the connection of the apparatus with the port, stabilizes the device against off-axis moments, and/or prevents kinking or damaging of the device.

Reference will now be made in detail to embodiments and aspects of the present disclosure, examples of which are illustrated in the accompanying drawings. Where possible, the same reference numbers will be used throughout the drawings to refer to the same or like parts.

Figure 2:
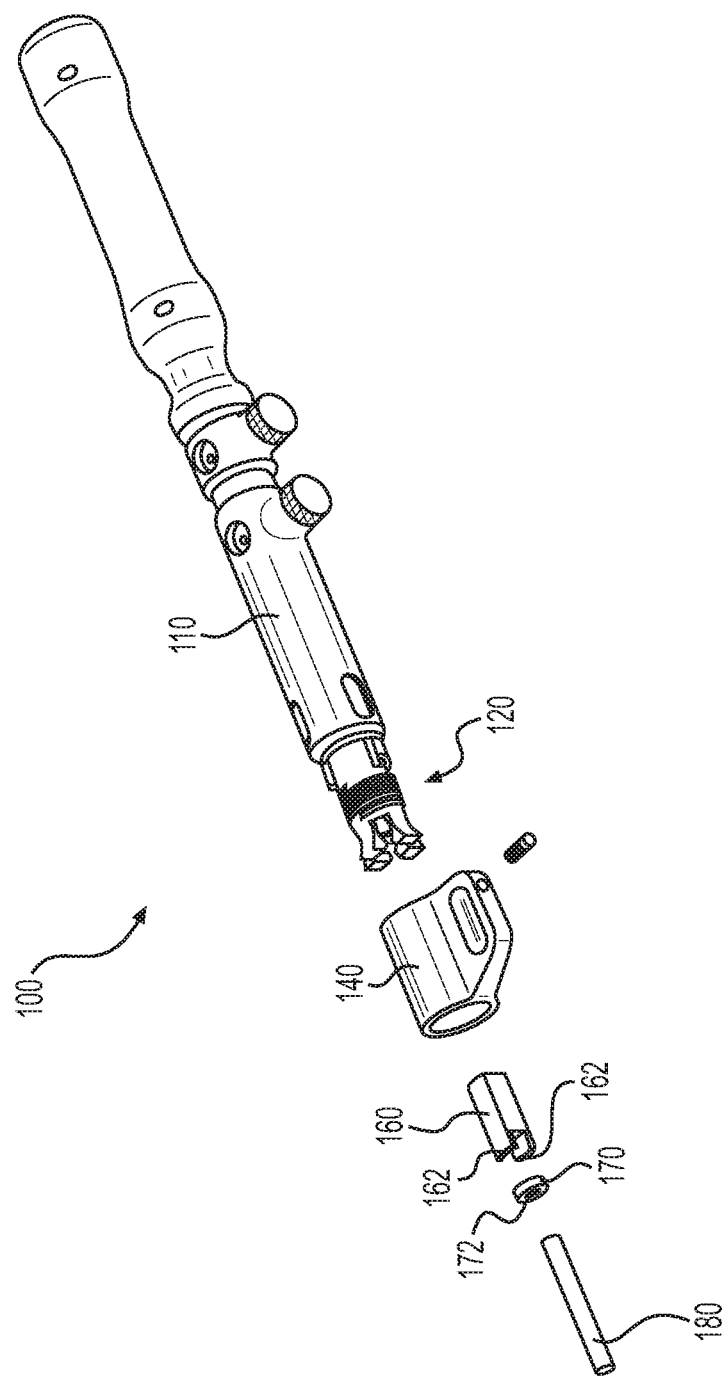
FIG. 2 is a component view of the exemplary apparatus of FIG. 1, according to embodiments of the present disclosure.

FIG. 1 is a perspective view of an exemplary apparatus 100 for connecting or mounting a device (not shown) to an exemplary endoscope 200 (partially shown). FIG. 2 is a component view of apparatus 100. As shown in FIGS. 1 and 2, apparatus 100 is configured to connect to an exemplary port 220 of endoscope 200. Port 220 may be a biopsy port providing a device access to a working channel 210 of endoscope 200. The device to be connected may be desirably selected for performing a suitable endoscopic procedure. As described herein, apparatus 100 may be an integral component of the device or may connect to the device via any suitable type of connection. When apparatus 100 is securely connected to port 220, the device or the shaft of the device may extend through port 220 and into working channel 210. Port 220 may be normally closed by a biopsy port cap before use.

Apparatus 100 may include a plurality of components that allow for secured connection of a desired device to port 220 in an efficient and effective manner. As shown in FIG. 2, apparatus 100 may include a multi-tined connector 120, a locking sleeve 140, and an anti-rotational key 160. Multi-tined connector 120 includes a lumen extending therethrough (not shown), providing a passage for the desired device. Multi-tined connector 120 is configured to engage with or disengage from port 220 based on the position of locking sleeve 140. Locking sleeve 140 is configured to actuate the engagement of multi-tined connector 120 and lock the multi-tined connector 120 in an engaged position or in a disengaged position.

Anti-rotational key 160 is configured to orient apparatus 100 when connecting to port 220 and to prevent apparatus 100 from rotating around port 220 during and after the connection. Anti-rotational key 160 may be an integral part of multi-tined connector 120 or may be molded into multi-tined connector 120 or securely fitted within multi-tined connector 120 via friction fit, snap fit, etc. Anti-rotational key 160 has an elongated shape and a conduit therethrough (not shown) to provide passage to a device into port 220. To prevent apparatus 100 from rotating, anti-rotational key 160 may include a non-circular portion that extends over at least a section of its length.

Figure 7:
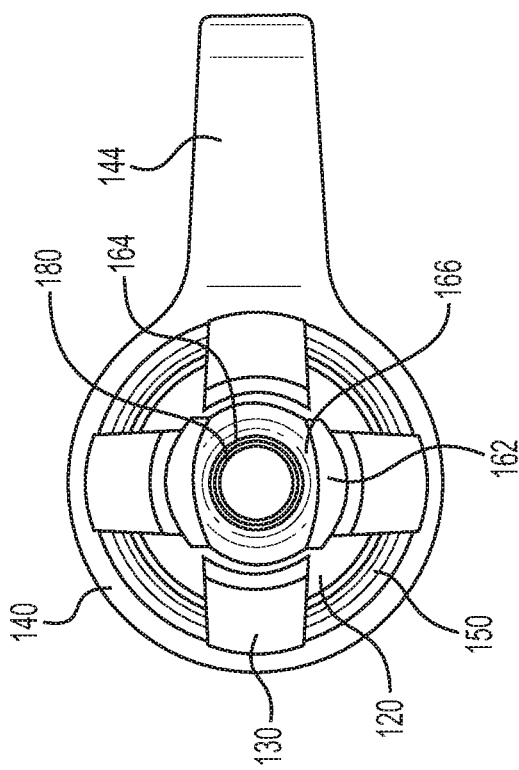
FIG. 7 is a bottom plan view of the exemplary apparatus of FIG. 1, according to embodiments of the present disclosure.

For example, as shown in FIG. 2, anti-rotational key 160 may have a pair of projections 162. When anti-rotational key 160 is received within multi-tined connector 120, projections 162 and the inner surface of multi-tined connector 120 define a non-circular pocket (pocket 166 as shown in FIG. 7) complementary to the flange of port 220. When the flange of port 220 has a non-circular shape, the non-circular pocket prevents the rotation of apparatus 100 and a device connected to apparatus 100 relative to port 220. Thus, anti-rotational key 160 further reduces the formation and/or accumulation of rotational torque in the device and prevents loosening of the connection of the device to port 220. To prevent deflection or deformation due to rotational forces, anti-rotational key 160 is made of a hard material, such as a hard plastic or metal.

As shown in FIG. 2, in some embodiments, apparatus 100 may further include a handle 110. Handle 110 may include at least one segment and a lumen (not shown) axially extending therethrough for receiving the device to be connected to port 220. The lumen of handle 110 aligns with that of multi-tined connector 120 such that the device may be inserted through apparatus 100 into port 220. As described herein, handle 110 may connect to multi-tined connector 120 via any suitable connection mechanism. For example, handle 110 may be fixedly, slidably, and/or removably connected to multi-tined connector 120.

As shown in FIG. 2, in some embodiments, apparatus 100 may further include a seal 170. Seal 170 is made of a compressible material, and may be sized and shaped to be positioned within multi-tined connector 120. A channel 172 is provided through seal 170 and connected with the lumen (not shown) extending through multi-tined connector 120, providing a device access to port 220 and working channel 210. Seal 170 may be compressed by port 220 when multi-tined connector 120 engages with port 220, thereby creating a fluid-tight seal against port 220 so that fluid does not leak out from working channel 210 or vacuum within working channel 210 can be maintained when desired. When compressed against port 220, seal 170 may also frictionally engage with port 220, thereby preventing the rotation of apparatus 100 about port 220.

As shown in FIG. 2, in some embodiments, apparatus 100 may further include a hollow conduit 180. Hollow conduit 180 may be fitted within anti-rotational key 160 and connected with the lumen (not shown) extending through multi-tined connector 120, providing a device access to the working channel 210. Hollow conduit 180 is made of a hard material, such as a hard, rigid plastic or metal, such that a device passing through hollow conduit 180 is prevented from being damaged or kinked during the connection to port 220 or use in an endoscopic procedure. As described herein, hollow conduit 180 may have an elongated shape and any suitable cross-sectional shape. For example, hollow conduit 180 may be an elongated tube with a circular or non-circular cross-section.

Figure 3:
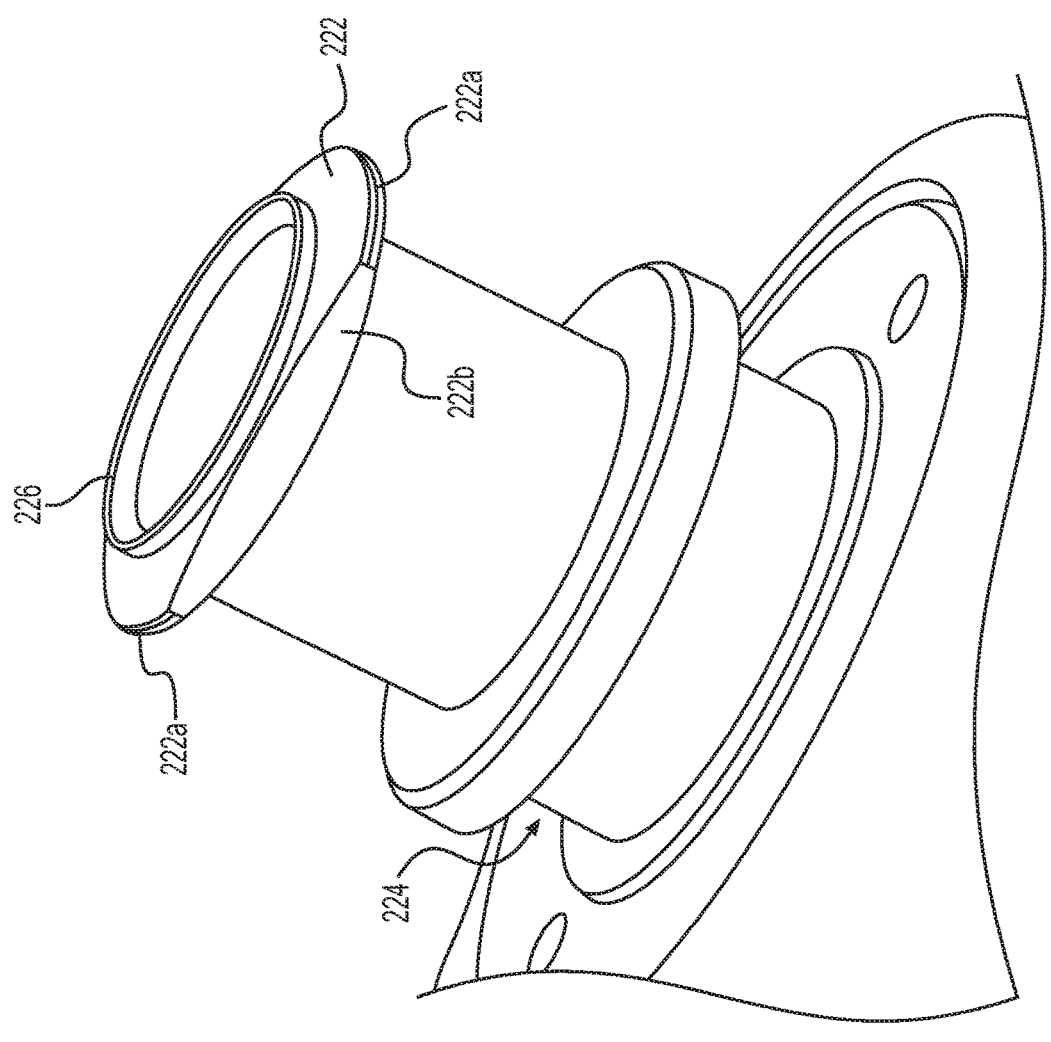
FIG. 3 is an enlarged perspective view of an exemplary port of an endoscope, according to embodiments of the present disclosure.

FIG. 3 is an enlarged perspective view of an exemplary port 220 of endoscope 200. As shown in FIG. 3, port 220 may include a flange 222. Flange 222 may have a non-circular shape. For example, flange 222 may have two protruding portions 222a opposing each other and two flat surfaces 222b. Flange 222 may further include a circular lip 226 on the top. A non-circular flange 222 may only be capable of being received or fitted in multi-tined connector 120 when multi-tined connector 120 is aligned to port 220 in the desired orientation. Advantageously, this required alignment prevents inadvertent connection of apparatus 100 in the wrong orientation and/or prevents apparatus 100 from rotating around port 220 after the connection.

In some embodiments, port 220 may further include a groove 224. Tines 130 may surround groove 224 when apparatus 100 is attached to port 220. When tines 130 are radially deflected inward by locking sleeve 140, tines 130 may engage with groove 224, and tighten around and clamp onto groove 224. In other embodiments, port 220 may not have groove 224. In such instances, when tines 130 are radially deflected inward by locking sleeve 140, tines 130 may tighten around the outer surface of port 220, forming a friction fit around port 220 as further described below with reference to FIGS. 13-16.

Details of exemplary structures of the components of apparatus 100 and exemplary mechanisms for securely connecting apparatus 100 to port 220 are further described below.

Figure 4A:
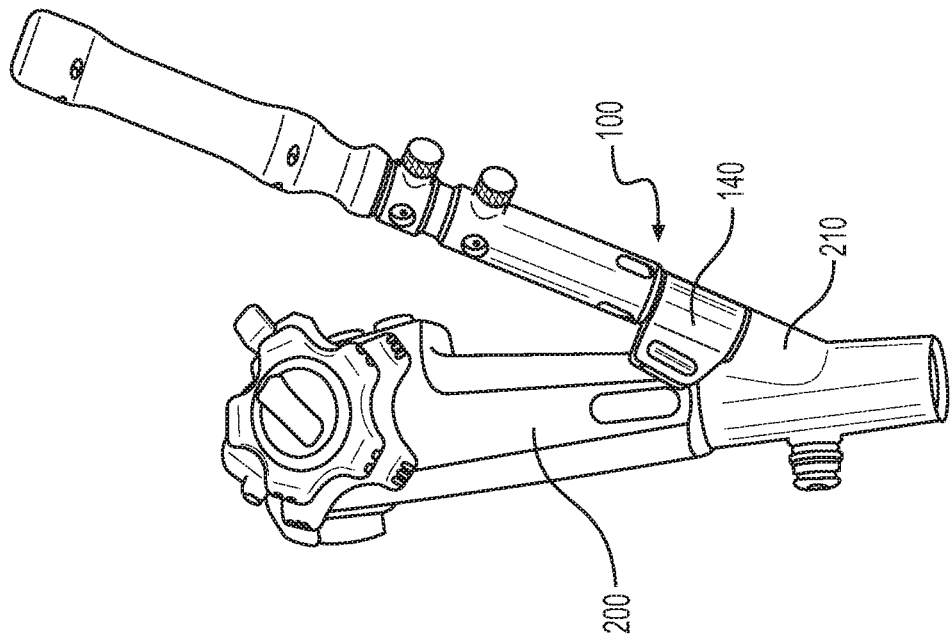
FIG. 4A is a perspective view of the exemplary apparatus of FIG. 1, connected to an exemplary port of an endoscope in an unlocked position, according to embodiments of the present disclosure.
Figure 4B:
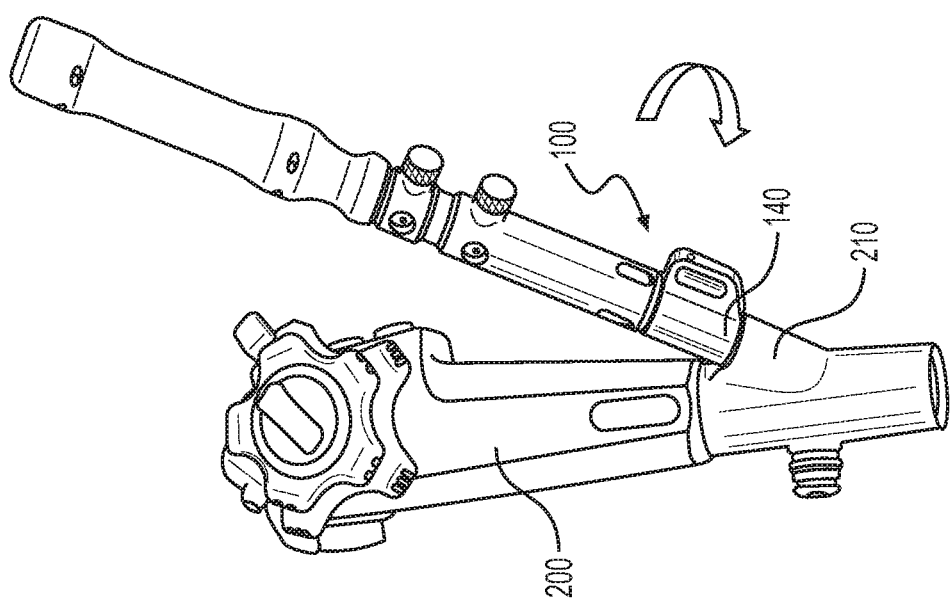
FIG. 4B is a perspective view of the exemplary apparatus of FIG. 1, connected to an exemplary port of an endoscope in a locked position, according to embodiments of the present disclosure.

FIGS. 4A and 4B illustrate the connection of an exemplary embodiment of apparatus 100 to port 220 (not shown) of endoscope 200. As shown in FIGS. 4A and 4B, locking device 140 operates in two positions, an unlocked position, as shown in FIG. 4A, and a locked position, as shown in FIG. 4B. When locking device 140 is in the locked position, multi-tined connector 120 is securely engaged with port 220 and locked in the engaged position. When locking device 140 is in the unlocked position, multi-tined connector 120 is disengaged from port 220. The binary nature of the switch removes uncertainty as to if/when the locked or unlock position is reached. This in turn reduces the possibility of damaging or kinking the device during the connection, disconnection, and/or usage of the device, thereby improving the efficiency and effectiveness of an endoscopic procedure. Exemplary structures and working mechanisms of apparatus 100 for achieving the binary operation of locking sleeve 140 are described further below with reference to FIGS. 8-10.

Figure 5:
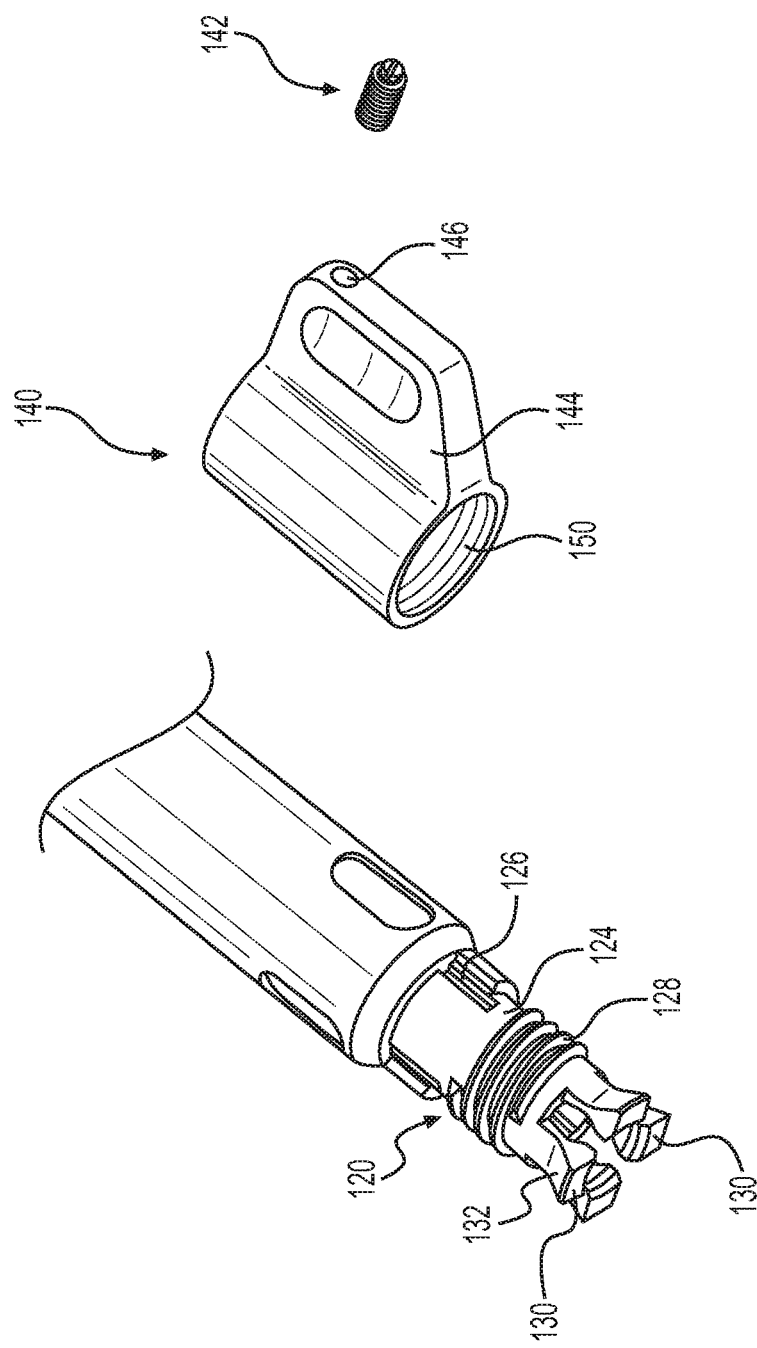
FIG. 5 is an enlarged view of exemplary components of the exemplary apparatus of FIG. 1, according to embodiments of the present disclosure.
Figure 6:
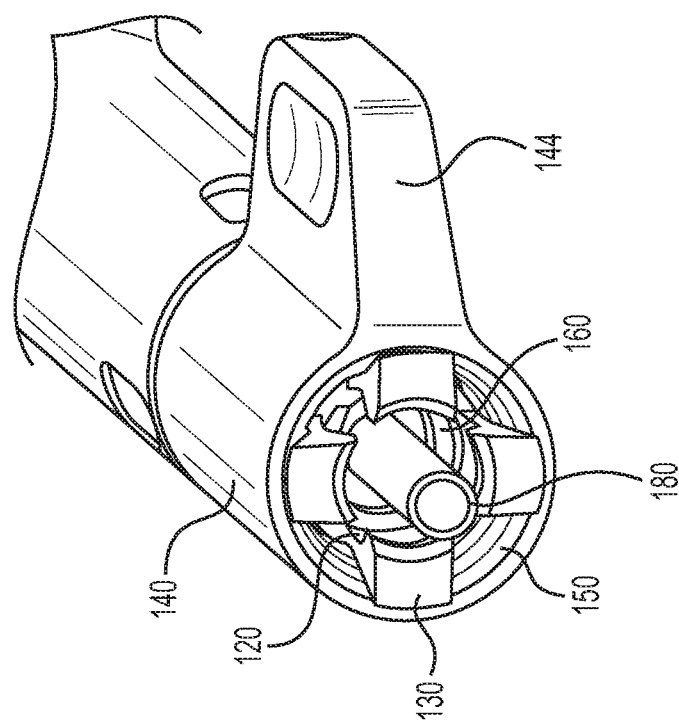
FIG. 6 is a partial perspective view of the exemplary apparatus of FIG. 1, according to embodiments of the present disclosure.

FIG. 5 is an enlarged view of exemplary components of apparatus 100. FIG. 6 is a partial perspective view and FIG.

7 is a bottom plan view of apparatus 100. As shown in FIGS. 5-7, multi-tined connector 120 includes a body portion 124 and a plurality of tines 130 for engaging with port 220. Body portion 124 includes an outer locking interface 128 and a lumen (not shown) axially extending therethrough for receiving a device. Tines 130 may be evenly radially spaced apart. When there are an even number of tines 130, tines 130 may be arranged in one or more pairs opposing one another. To engage with port 220, tines 130 may be actuated to radially deflect inward by switching locking sleeve 140 from the unlocked position to the locked position. To disengage with port 220, tines 130 may be released to radially deflect outward by switching locking sleeve 140 from the locked position to the unlocked position.

Locking sleeve 140 includes an inner engagement surface 150 for actuating tines 130 to engage with port 220. Inner engagement surface 150 may be a normally cylindrical inner surface or a conical inner surface that matches or rides outer tapered surfaces 132 of tines 130. When locking sleeve 140 is moved axially along multi-tined connector 120 towards tines 130, inner engagement surface 150 squeezes outer tapered surfaces 132, causing tines 130 to radially deflect inward. Such inward deflection of tines 130 causes tines 130 to tighten around and clamp onto port 220.

Figure 11:
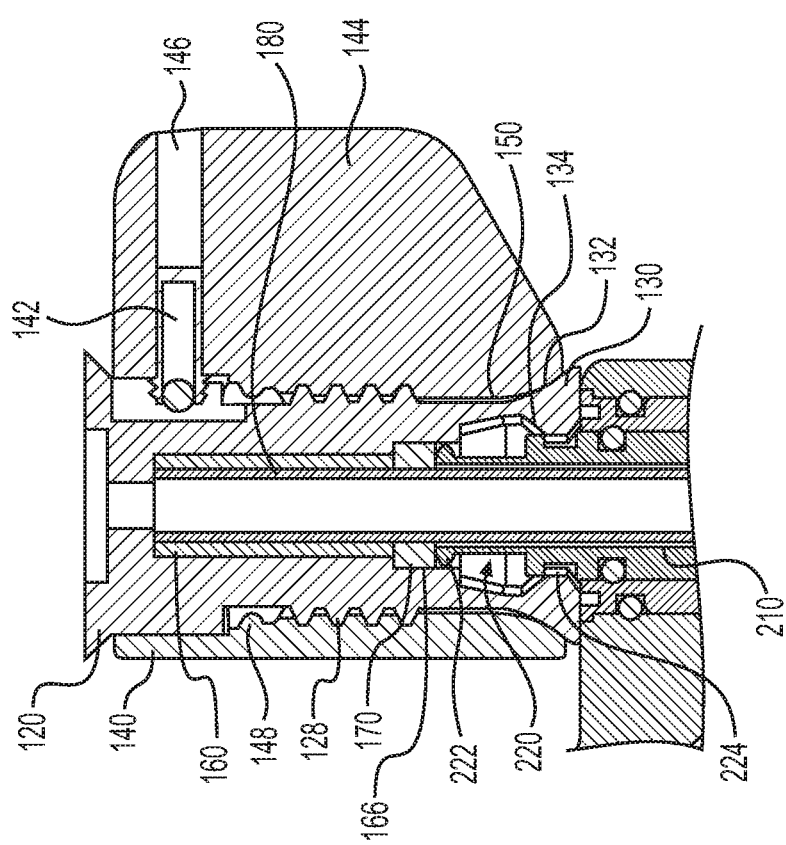
FIG. 11 is a perpendicular cross-sectional view of the exemplary apparatus of FIG. 1 connected to the exemplary port of FIG. 3 in an unlocked position, according to embodiments of the present disclosure.
Figure 18:
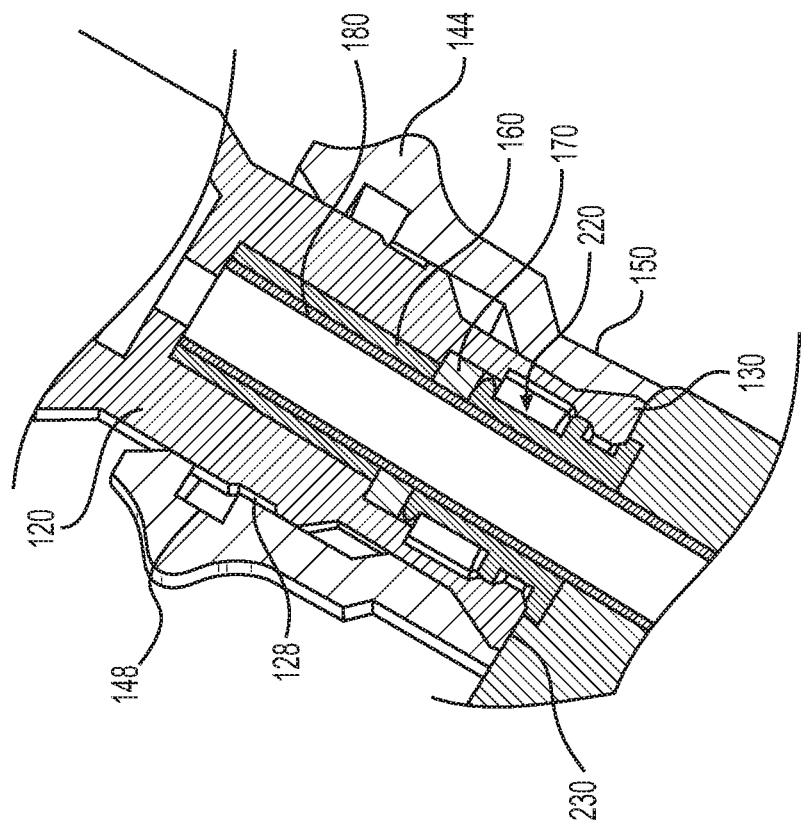
FIG. 18 is a perpendicular cross-sectional view of the exemplary apparatus of FIG. 17 connected to the exemplary port of FIG. 3, according to embodiments of the present disclosure.
Figure 17:
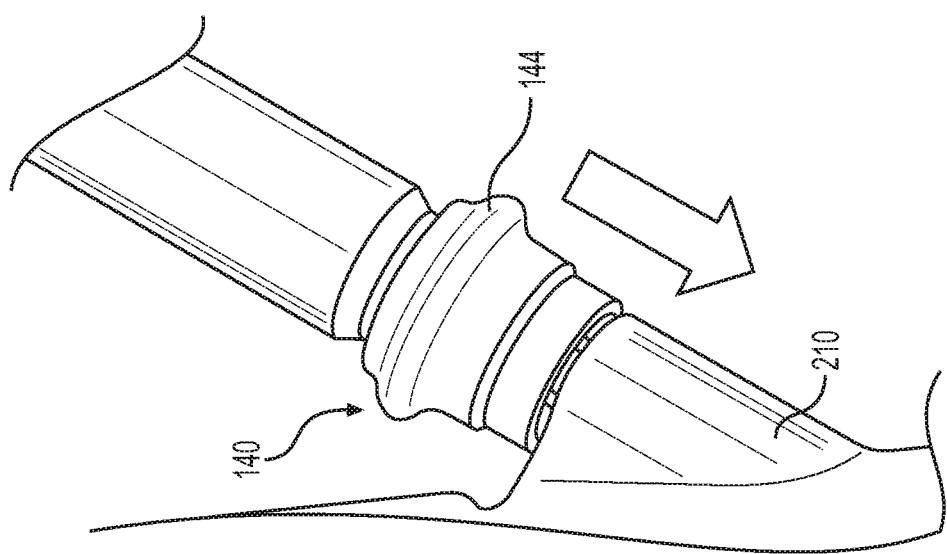
FIG. 17 is a partial perspective view of another exemplary apparatus for connecting a device to an exemplary port of an endoscope.

Locking sleeve 140 further includes an inner locking interface (inner locking interface 148 as shown in FIG. 11) for interlocking with outer locking interface 128 of multi-tined connector 120. As shown in FIGS. 5-7, the interlocking of locking sleeve 140 and multi-tined connector 120 may use a threaded mechanism or a snap-fit mechanism (as shown in FIGS. 17 and 18) to switch locking sleeve 140 between the locked position and unlocked position, which in turn switches tines 130 to in an engaged position or in a disengaged position. For example, locking sleeve 140 may be moved in the axial direction by rotating locking sleeve 140 relative to multi-tined connector 120 in the clockwise or counterclockwise direction. A desired range of axial movement of locking sleeve 140 for actuating tines 130 to engage with port 220 is achieved by rotating locking sleeve 140 from the unlocked position to the locked position.

In some embodiments, outer locking interface 128 may include a multi-lead thread to interlock with a complementary thread of locking sleeve 140. The multi-lead thread may have a predetermined number and/or pitch of threads such that a desired range of axial movement of locking sleeve 140 can be achieved by a partial rotation of locking sleeve 140 clockwise or counterclockwise. In some embodiments, the number and/or pitch of the multi-lead thread of outer locking interface 128 are predetermined to allow a physician to accomplish the switching of locking sleeve 140 by an intuitive and/or convenient rotation of locking sleeve 140 while still achieving a desired axial movement and adequate frictional threaded engagement. For example, locking sleeve 140 may rotate for a predetermined degree ranging from 30° to 330°, such as 45°, 60°, 90°, or 120°, to achieve a desired axial movement for actuating tines 130 to engage with port 220 and adequate frictional threaded engagement for locking tines 130 in the engaged position.

In some embodiments, as shown in FIGS. 5-7, locking sleeve 140 further includes a single-hand control handle 144 to switch locking sleeve 140 between locked and unlocked positions. Handle 144 allows a physician to operate locking sleeve 140, and thus the engagement of tines 130 with port 220, using one hand. The physician may use the other hand for holding, controlling, or stabilizing a device or an endoscope, thereby improving the efficiency and/or effectiveness of an endoscopic procedure. Handle 144 may also provide a visual cue that indicates the current position of locking sleeve 140 to a physician. Advantageously, this visual cue allows the physician to promptly secure the connection of apparatus 100 and a device to port 220, thereby reducing the possibility of undesirable displacement of the device and improving the efficacy of the endoscopic procedure.

In some embodiments, as shown in FIGS. 2 and 7, anti-rotational key 160 has a pair of projections 162 and a conduit 164 extending throughout its length to provide passage to a device to port 220. As shown in FIG. 7, when anti-rotational key 160 is received within multi-tined connector 120, opposing projections 162 and the inner surface of multi-tined connector 120 define a non-circular pocket 166 that matches the periphery of flange of port 220. Advantageously, when the flange of port 220 has a non-circular periphery, non-circular pocket 166 prevents the rotation of apparatus 100, and thus the rotation of the device connected to apparatus 100 relative to port 220.

Apparatus 100 further includes a detent arrangement configured to hold locking sleeve 140 at the locked position or at the unlocked position. The detent arrangement may be provided by any suitable mechanical structures provided on multi-tined connector 120 and locking sleeve 140. Advantageously, the detent arrangement defines the binary operation of locking sleeve 140 between the locked and unlocked positions, improving the efficiency and effectiveness of the connection of a device during an endoscopic procedure.

Figure 8:
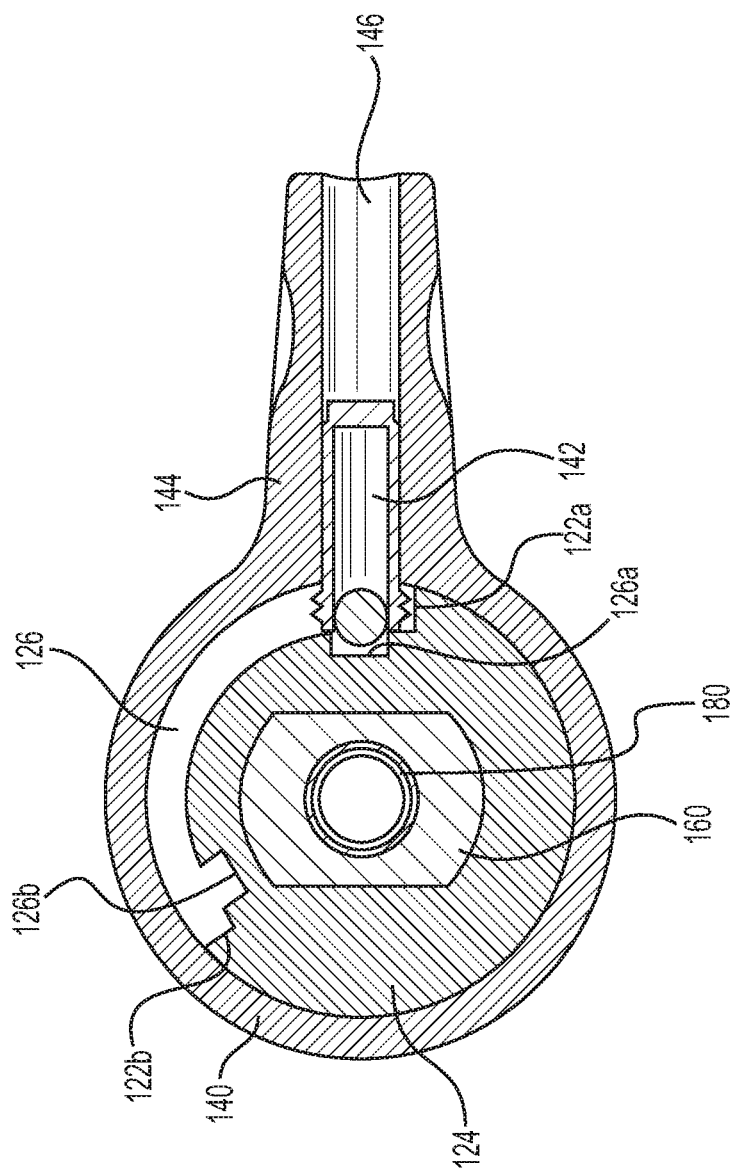
FIG. 8 is a parallel cross-sectional view of an exemplary detent arrangement of the exemplary apparatus of FIG. 1, according to embodiments of the present disclosure.

FIG. 8 is a parallel cross-sectional view of apparatus 100. As shown in FIG. 8, in some embodiments, apparatus 100 includes a ball detent arrangement. For example, locking sleeve 140 includes a spring-loaded ball 142 and a bored cylinder 146. Spring-loaded ball 142 is capable of sliding against the pressure of the spring. Multi-tined connector 120 includes a detent 126 having two recesses 126a and 126b. When spring-loaded ball 142 is aligned with recess 126a, spring-loaded ball 142 falls partially into the recess under spring pressure, holding locking sleeve 140 at the unlocked position. When additional force is applied to the locking sleeve 140, e.g., pressure on handle 144 to rotate locking sleeve 140, spring-loaded ball 142 can be pushed back into bored cylinder 146. This further compresses the spring and allows spring-loaded ball 142 to be moved towards and aligned with recess 126b, thereby moving locking sleeve 140 to the locked position.

In some embodiments, as shown in FIG. 8, multi-tined connector 120 further includes two hard stops 122a and 122b to restrict the movement of locking sleeve 140 to be within a range between the locked and unlocked positions. Advantageously, the detent arrangement and/or the hard stops 122a and 122b prevent locking sleeve 140 from rotating beyond the locked or unlocked positions, and thus may further reduce or prevent the accumulation of rotational torque in the shaft of a device connected to apparatus 100. The detent arrangement and/or the hard stops thus may further prevent loosening of the connection of apparatus 100 and the device connected to apparatus 100 from port 220. Additionally, by holding the position of locking sleeve 140 either at the locked position or at the unlocked position, the detent arrangement and/or the hard stops prevent ambiguity as to whether locking sleeve 140 has reached the desired position.

Figure 10:
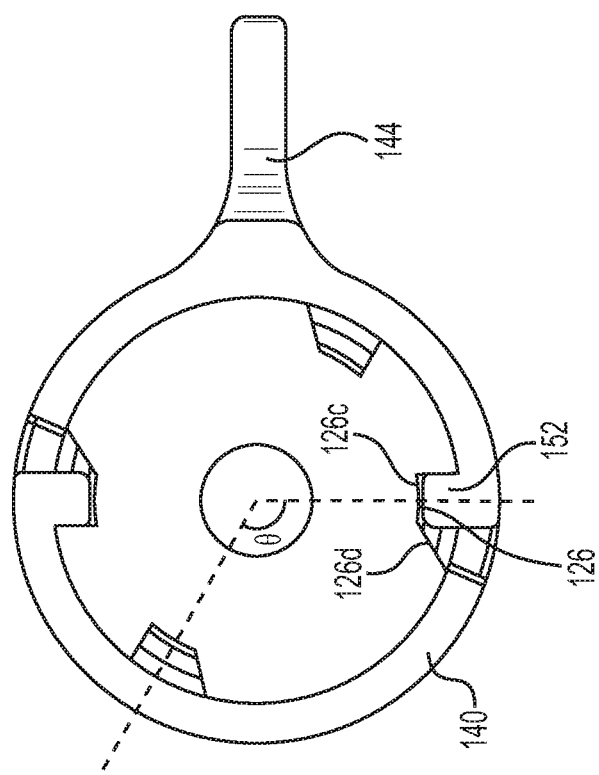
FIG. 10 is a parallel cross-sectional view of the exemplary detent arrangement of FIG. 9, according to embodiments of the present disclosure.
Figure 9:
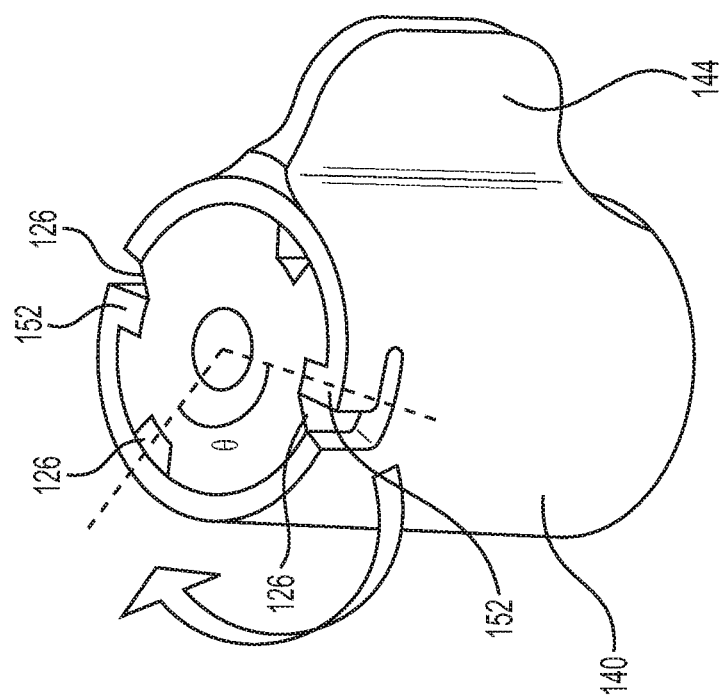
FIG. 9 is a partial perspective view of another exemplary detent arrangement of the exemplary apparatus of FIG. 1, according to embodiments of the present disclosure.

FIG. 9 is a partial perspective view of another exemplary detent arrangement of apparatus 100. FIG. 10 is a parallel cross-sectional view of the exemplary detent arrangement FIG. 10. As shown in FIGS. 9 and 10, in some embodiments, the detect arrangement of apparatus 100 is provided by one or more integral detent flexures 152 of locking sleeve 140.

Multi-tined connector 120 includes one or more detents 126 to capture the detent flexures 152. As shown in FIG. 10, detents 126 may each have a perpendicular opening 126c and an angular opening 126d. Perpendicular opening 126c is configured to capture detent flexure 152 and operates as a hard stop, preventing locking sleeve 140 from rotating in the counterclockwise direction, for example. Angular opening 126d is configured to capture detent flexure 152, but allows detent flexure 152 to move out by moving locking sleeve 140 in a clockwise direction. For example, when additional force is applied to the locking sleeve 140 in the unlocked position, e.g., pressure on handle 144 to rotate locking sleeve 140 in the clockwise direction, detent flexure 152 can be pushed out of angular opening 126d of a first detent 126 corresponding to the unlocked position, thereby allowing locking sleeve 140 to be moved towards the locked position. Similarly, when additional force is applied to the locking sleeve 140 in the locked position in the clockwise direction, detent flexure 152 can be pushed out of angular opening 126d of a second detent 126 corresponding to the locked position, thereby allowing locking sleeve 140 to be moved towards the unlocked position.

As shown in FIGS. 9 and 10, apparatus 100 may include one or more pairs of detent 126 and detent flexure 152 to hold locking sleeve 140 in the unlocked or locked position. Continuous partial rotation of locking sleeve 140 in a clockwise direction, for example, may switch locking sleeve 140 from unlocked position to locked position, and then to unlocked position again. As shown in FIGS. 9 and 10, the angle of partial rotation by locking sleeve 140 from the unlocked position to the locked position, and vice versa, is represented by θ. As described above, the multi-lead thread of multi-tined connector 120 may have a predetermined number and/or pitch of threads such that a partial rotation of locking sleeve 140 may achieve a desired range of axial movement of locking sleeve 140. In such instances, θ may range from 30° to 330°.

As described above, other suitable detent arrangement may be used for holding locking sleeve 140 at the locked position or the unlocked position. In one exemplary embodiment, a detent arrangement of apparatus 100 may use a locking pin and groove configuration (not shown). For example, multi-tined connector 120 may include a groove having two recesses or stops corresponding to the locked and unlocked positions of locking sleeve 140. The locking pin may be inserted through locking sleeve 140 to engage with a recess or a stop of the groove of multi-tined connector 120 so as to hold locking sleeve 140 at the corresponding locked or unlocked position. In another exemplary embodiment, a detent flexure of locking sleeve 140 may be made of a compressible material. Locking sleeve 140 may be held at the locked position or the unlocked position by the deformation of the detent flexure.

Figure 12:
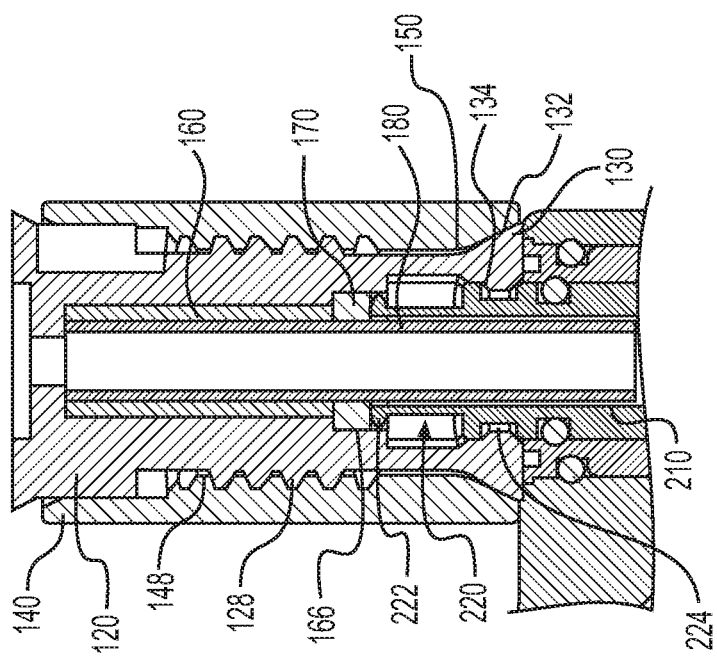
FIG. 12 is a perpendicular cross-sectional view of the exemplary apparatus of FIG. 1 connected to the exemplary port of FIG. 3 in a locked position, according to embodiments of the present disclosure.

Exemplary mechanisms for securely connecting apparatus 100 to port 220 are further described below with reference to FIGS. 11 and 12. FIG. 11 is a perpendicular cross-sectional view of apparatus 100 connected to port 220 of FIG. 3 in an unlocked position. FIG. 12 is a perpendicular cross-sectional view of apparatus 100 connected to port 220 in a locked position.

As shown in FIG. 11, when apparatus 100 is connected to port 220 in the unlocked position, port 220 is received within multi-tined connector 120. Locking sleeve 140 is at the unlocked position. Anti-rotational key 160 resides within multi-tined connector 120. Flange 222 of port 220 is aligned with and received within pocket 166 defined by opposing projections 162 (not shown) of anti-rotational key 160 and the inner surface of multi-tined connector 120. Outer locking interface 128 of multi-tined connector 120 includes a multi-lead thread that engages with a complementary thread of inner locking interface 148 of locking sleeve 140. Tines 130 of multi-tined connector 120 surround groove 224 of port 220, ready to engage with and clamp onto groove 224 of port 220.

As shown in FIG. 12, when locking sleeve 140 is switched to the locked position, locking sleeve 140 is moved axially along multi-tined connector 120 towards tines 130 such that inner engagement surface 150 of locking sleeve 140 squeezes outer tapered surface 132 of tines 130, causing tines 130 to radially deflect inward. Such inward deflection of tines 130 in turn causes tines 130 to tighten around and clamp onto port 220. For example, as shown in FIGS. 11 and 12, tines 130 may include inner ridges 134 with inclined surfaces. As tines 130 radially deflect inward, inner ridges 134 of tines 130 engage with and pull groove 224 of port 220 into multi-tined connector 120, and further tighten around groove 224. Such engagement of tines 130 with groove 224 of port 220 allows apparatus 100 to be securely locked onto port 220.

In some embodiments, as shown in FIGS. 11 and 12, seal 170 is sized and shaped to be positioned within pocket 166. Seal 170 can be compressed by port 220 when locking sleeve 140 moves from the unlocked position to the locked position, where port 220 is pulled into multi-tined connector 120. The compression of seal 170 creates a fluid-tight seal against port 220, e.g., against flange 222 and/or lip 226, to prevent fluid from leaking from working channel 210 and/or to maintain a vacuum within working channel 210 when desired. When compressed, seal 170 may also frictionally engage with port 220, thereby preventing the rotation of multi-tined connector 120 about port 220.

As shown in FIGS. 11 and 12, when apparatus 100 is connected to port 220, hollow conduit 180 is partially received within anti-rotational key 160 and partially received within port 220 and/or working channel 210, providing a passage for a device to be inserted into port 220 and/or working channel 210. Advantageously, hollow conduit 180 provides a guide for the connection of apparatus 100 with port 220, stabilizes a device passing therethrough against off-axis moments, and/or prevents kinking or damaging of the device during the connection of the device to the endoscope.

As described above, in some embodiments, port 220 may not have groove 224. In such instances, when tines 130 are radially deflected inward at a result of the axial movement of locking sleeve 140, tines 130 may instead tighten around the outer surface of port 220, engage with flange 222, and/or form a friction fit around port 220 as further described below with reference to FIGS. 13-16.

Figure 14:
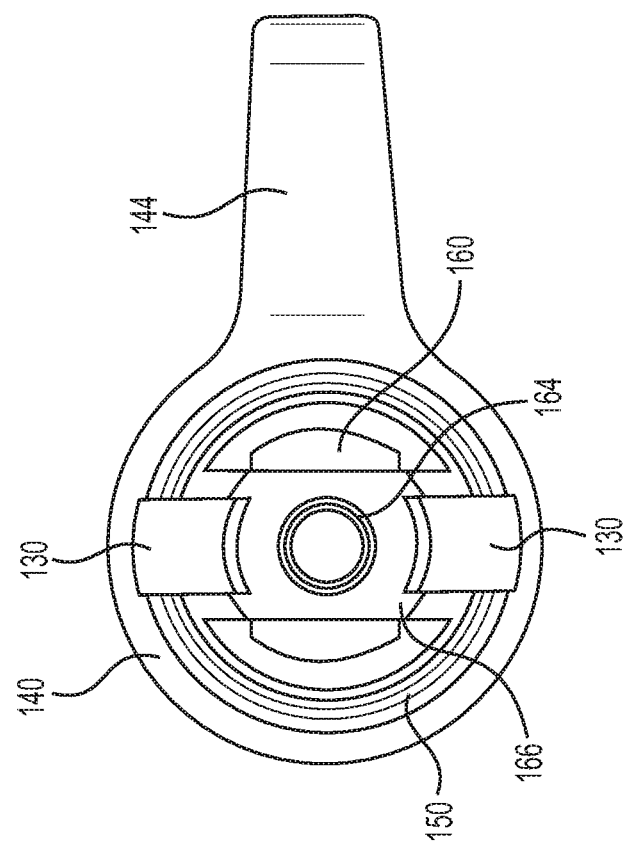
FIG. 14 is a bottom plan view of the exemplary apparatus of FIG. 13, according to embodiments of the present disclosure.
Figure 13:
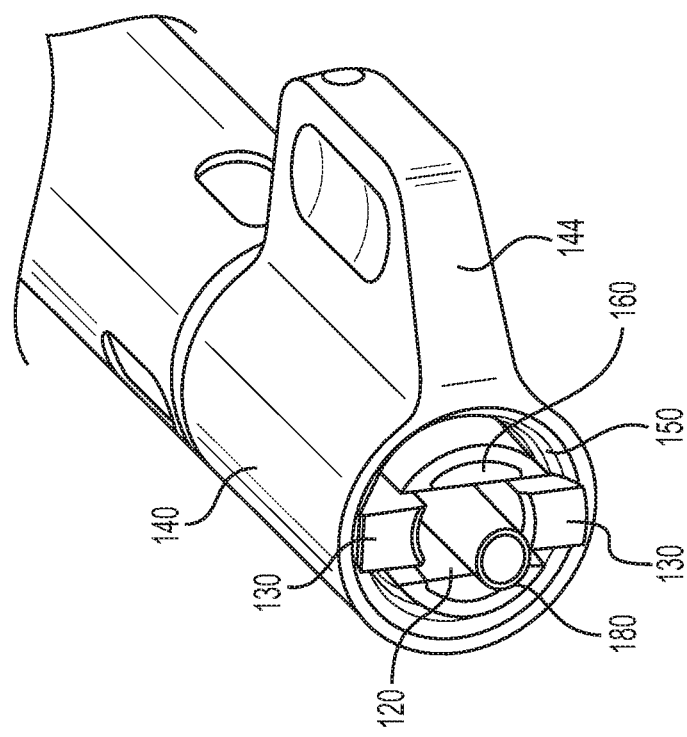
FIG. 13 is a partial perspective view of another exemplary apparatus for connecting a device to an exemplary port of an endoscope, according to embodiments of the present disclosure.

FIG. 13 is a partial perspective view of another exemplary apparatus 100. FIG. 14 is a bottom plan view of the exemplary apparatus 100 of FIG. 13. As shown in FIGS. 13 and 14, multi-tined connector 120 of apparatus 100 may include one or more tines 130 arranged in pairs opposing one another for engaging with port 220. To engage with port 220, tines 130 can be actuated to radially deflect inward by switching locking sleeve 140 from the unlocked position to the locked position. To disengage with port 220, tines 130 can be released to radially deflect outward by switching locking sleeve 140 from the locked position to the unlocked position.

Figure 16:
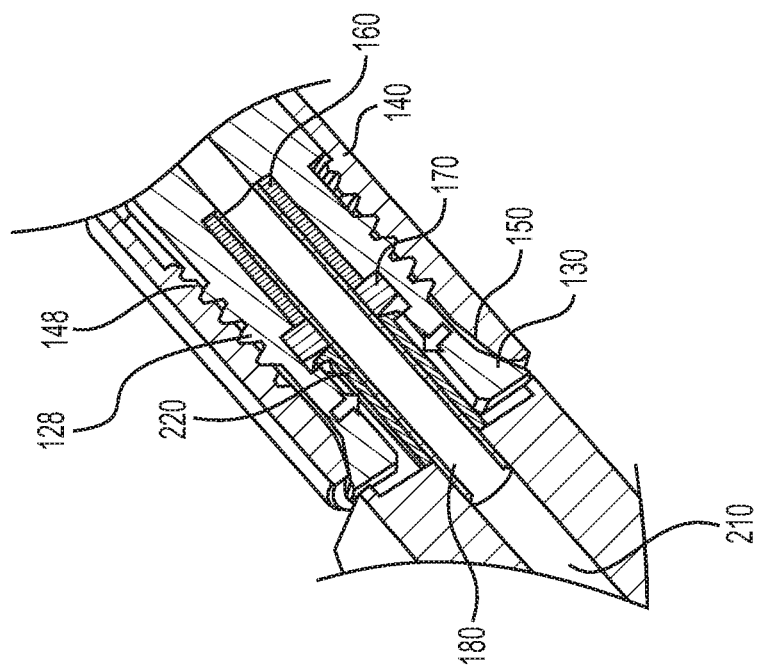
FIG. 16 is a perpendicular cross-sectional view of the exemplary apparatus of FIG. 13 connected to the exemplary port of FIG. 15, according to embodiments of the present disclosure.
Figure 15:
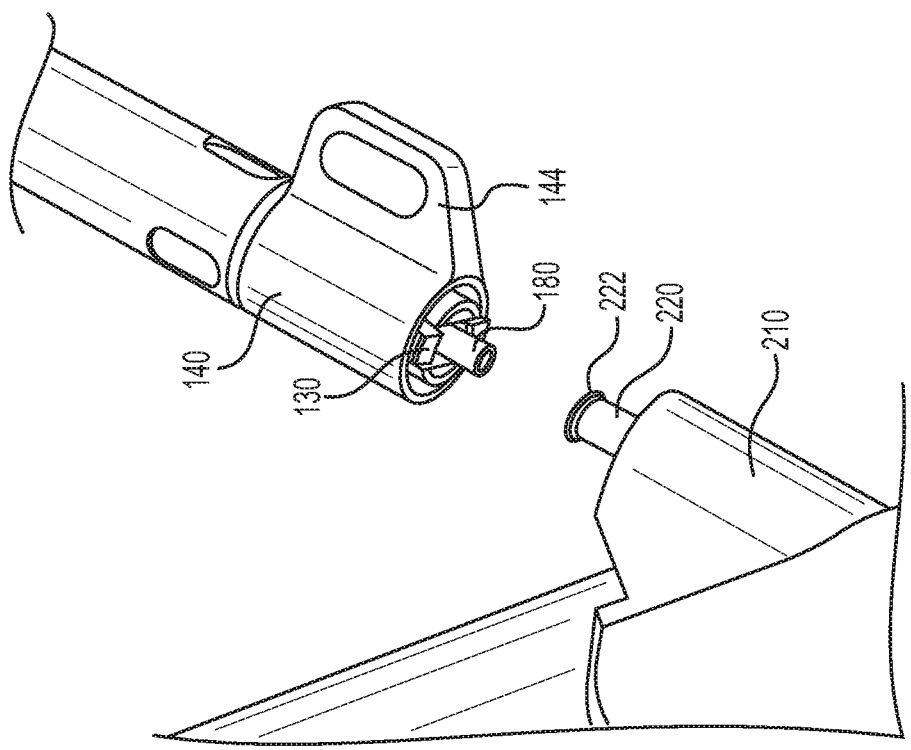
FIG. 15 is a partial perspective view of the exemplary apparatus of FIG. 13 to be connected to another exemplary port of an endoscope, according to embodiments of the present disclosure.

FIG. 15 is a partial perspective view of the exemplary apparatus 100 of FIG. 13 connecting to an exemplary port 220 without groove 224. FIG. 16 is a perpendicular cross-sectional view of the exemplary apparatus 100 of FIG. 13 connected to the exemplary port 220 of FIG. 15. As shown in FIGS. 15 and 16, when port 220 does not have groove 224, the radially inward deflection of tines 130 causes the inner surfaces of tines 130 to press against the outside wall of port 220 with sufficient force as indicated by the arrows shown in FIG. 16, thereby forming a friction fit with port 220. Advantageously, such friction fit allows apparatus 100 to be securely connected to port 220, and prevents apparatus 100 from rotating around port 220, which in turn prevents the accumulation of rotational torque in the device to be connected to port 220. In some embodiments, the inner surface of tines 130 and/or the outer surface of port 220 forming the friction fit are made of materials having high coefficients of friction to form a secured connection.

Additionally or alternatively, when port 220 does not have groove 224, tines 130 of multi-tined connector 120 may clamp onto flange 222. For example, when flange 222 has a non-circular shape as shown in FIG. 3, tines 130 may engage with and clamp onto protruding portions 222a of flange 222 to securely lock apparatus 100 onto port 220.

FIGS. 17 and 18 illustrate another exemplary mechanism of apparatus 100 for achieving the binary operation of locking sleeve 140. As shown in FIGS. 17 and 18, locking sleeve 140 is placed at least partially over multi-tined connector 120. Sliding locking sleeve 140 axially along multi-tined connector 120 allows locking sleeve 140 to switch between the unlocked and locked positions.

For example, outer locking interface 128 of multi-tined connector 120 and inner locking interface 148 of locking sleeve 140 may include complementary fitting structures with two operational stops, corresponding to the unlocked position and locked position of locking sleeve 140 respectively. Sliding locking sleeve 140 from the unlocked position toward port 220 as indicated by the arrow in FIG. 17 causes tines 130 to be squeezed or compressed by inner engagement surface 150 of locking sleeve 140. This in turn causes tines 130 to radially deflect inward and engage with port 220 as described above. When locking sleeve 140 is at the locked position, the interaction of the bottom of locking sleeve 140 and the top surface 230 of the endoscope around biopsy port 220 further increases the stability of the connection of apparatus 100 to port 220. Sliding locking sleeve 140 away from port 220 releases tines 130 from being compressed by inner engagement surface 150 of locking sleeve 140. This in turn disengages tines 130 from port 220.

This exemplary binary switching configuration of locking sleeve 140 allows a physician to securely connect or disconnect a device using one hand while freeing up the other hand for holding or stabilizing the device or the endoscope. In such instances, handle 144 may have a suitable shape to facilitate the application of pressure for actuating the axial sliding of locking sleeve 140. For example, as shown in FIGS. 17 and 18, handle 144 may provide a platform surrounding the body of locking sleeve 140 to facilitate the switching of the position of locking sleeve 140 using one hand.

The complementary fitting structures of multi-tined connector 120 and locking sleeve 140 may use any suitable detent arrangement for holding locking sleeve 140 at the locked position or at the unlocked position, such as a ball detent arrangement, a canted coil spring and groove arrangement, and integral detent flexure arrangement. In a ball detent arrangement, one of locking sleeve 140 and multi-tined connector 120 may include one or more spring-loaded balls while the other may include two bored grooves axially separated apart. When the spring-loaded balls are aligned with and received within a bored groove, locking sleeve 140 is held at the locked or unlocked position corresponding to that groove. In a canted coil spring and groove arrangement, outer locking interface 128 of multi-tined connector 120 may include a canted coil spring at least partially received within a housing of outer locking interface 128. The inner locking interface 148 of locking sleeve 140 may include two grooves for retaining the canted coil spring, corresponding to the locked position and unlocked position of locking sleeve 140 respectively. In the integral detent flexure arrangement, locking sleeve 140 may have one or more detent flexures. Multi-tined connector 120 may include one or more detents to capture the detent flexures at two axial locations, corresponding to the locked position and unlocked position of locking sleeve 140 respectively.

As described herein, apparatus 100 may be configured as a separate connector or an integrated component of a device to be connected to an endoscope. Any combination of the various features of apparatus 100 described above may be incorporated into a device or an endoscope as an integral component thereof.

The various components of apparatus 100 may be fabricated from any suitable materials employing any suitable manufacturing processes. For example, the components may be fabricated from plastic materials (such as ABS, Nylon, polysulfone, polycarbonate, polypropylene, polyetherimide, TEFLON, acetal copolymer, silicone), composite materials (such as glass filled plastics, carbon fiber or thermoplastic elastomers, metallic materials (such as stainless steel, aluminum, titanium), and various combinations thereof.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An apparatus for connecting a device to an endoscope, the apparatus comprising:
   a multi-tined connector configured to engage with a port of an endoscope having a non-circular flange, the multi-tined connector comprising:
      a body portion having a lumen axially extending therethrough and an outer locking interface; and
      a plurality of tines connected to the body portion, the tines having outer tapered surfaces, being radially deflectable, and operating between an engaged position and a disengaged position,
      wherein in the engaged position, the tines engage with the port;
   a locking sleeve operating between a locked position and an unlocked position, the locking sleeve comprising:
      an inner engagement surface; and
      an inner locking interface configured to engage with the outer locking interface;
      wherein in the locked position, the locking sleeve holds the tines in the engaged position, and in the unlocked position, the locking sleeve leaves the tines in the disengaged position; and
   an anti-rotational key integral to or received within the lumen of the body portion of the multi-tined connector.

2. The apparatus of claim 1, wherein when the locking sleeve moves from the unlocked position to the locked position, the inner engagement surface of the locking sleeve engages with the outer tapered surfaces of the tines to radially deflect the tines inward to engage with the port.

3. The apparatus of claim 1, wherein the anti-rotational key further comprises two opposing projections that, together with the surface of the lumen of the body portion, define a pocket for receiving the non-circular flange of the port, an inner perimeter of the pocket substantially matching the periphery of the non-circular flange.

4. The apparatus of claim 1, wherein the non-circular flange comprises at least one protruding portion.

5. The apparatus of claim 1, wherein the port further comprises a groove.

6. The apparatus of claim 5, wherein the tines further comprise inner ridges with inclined surfaces such that when the tines radially deflect inward, the inclined surfaces pull the groove of the port into the multi-tined connector and tighten around the groove.

7. The apparatus of claim 1, wherein when the tines radially deflect inward, inner surfaces of the tines press against and form a friction fit with an outside wall of the port.

8. The apparatus of claim 1, wherein the tines further comprise inner ridges with inclined surfaces such that when the tines radially deflect inward, the inclined surfaces engage with the non-circular flange.

9. The apparatus of claim 1, wherein the outer locking interface and the inner locking interface comprise complementary threads, and the pitch and/or number of the threads are predetermined such that the locking sleeve switches between the locked and unlocked positions by rotating for a predetermined degree.

10. The apparatus of claim 9, wherein the predetermined degree ranges from 30° to 330°.

11. The apparatus of claim 9, wherein the outer locking interface and the locking sleeve further comprise a detent arrangement for holding the locking sleeve at the locked position or at the unlocked position.

12. The apparatus of claim 9, wherein the outer locking interface comprises two or more hard stops predetermined at the locked position and unlocked position and configured to restrict movement of the locking sleeve to be within a range between the locked and unlocked positions.

13. The apparatus of claim 1, further comprising a hollow conduit at least partially received within the lumen of the body portion, wherein when the multi-tined connector is engaged with the port, the hollow conduit is at least partially received within the port.

14. The apparatus of claim 1, wherein
   the outer locking interface and the inner locking interface comprise complementary fitting structures with two operational stops, and
   the locking sleeve switches between the locked position and unlocked position by sliding along the multi-tined connector between the two operational stops.

15. The apparatus of claim 14, wherein the fitting structures comprise a detent arrangement for holding the locking sleeve at the locked position or at the unlocked position.

16. The apparatus of claim 1, further comprising a compressible seal configured to be compressed by the port when the multi-tined connector is engaged with the port.

17. The apparatus of claim 1, wherein the locking sleeve further comprises a handle to switch the locking sleeve between the locked position and the unlocked position.

18. The apparatus of claim 1, wherein the anti-rotational key comprising a conduit therethrough.

19. An endoscopic system comprising an apparatus for connecting a device to an endoscope, the apparatus comprising:
   a multi-tined connector to engage with a port of an endoscope having a non-circular flange, the multi-tined connector comprising:
      a body portion having a lumen axially extending therethrough and an outer locking interface; and
      a plurality of tines connected to the body portion, the tines having outer tapered surfaces, being radially deflectable, and operating between an engaged position and a disengaged position,
      wherein in the engaged position, the tines engage with the port;
   a locking sleeve operating between a locked position and an unlocked position, the locking sleeve comprising:
      an inner engagement surface; and
      an inner locking interface configured to engage with the outer locking interface;
      wherein in the locked position, the locking sleeve holds the tines in the engaged position, and in the unlocked position, the locking sleeve leaves the tines in the disengaged position; and
   an anti-rotational key integral to or received within the lumen of the body portion of the multi-tined connector.

20. A connector for engaging with a port having a non-circular flange, the connector comprising:
   a multi-tined connector to engage with a port having a non-circular flange, the multi-tined connector comprising:
      a body portion having a lumen axially extending therethrough and an outer locking interface; and
      a plurality of tines connected to the body portion, the tines having outer tapered surfaces, being radially deflectable, and operating between an engaged position and a disengaged position,
wherein in the engaged position, the tines engage with the port;
a locking sleeve operating between a locked position and an unlocked position, the locking sleeve comprising:
an inner engagement surface; and
an inner locking interface configured to engage with the outer locking interface;
wherein in the locked position, the locking sleeve holds the tines in the engaged position, and in the unlocked position, the locking sleeve leaves the tines in the disengaged position; and
an anti-rotational key integral to or received within the lumen of the body portion of the multi-tined connector.

* * * * *